US00PP31751P2

(12) United States Plant Patent
Whitcomb

(10) Patent No.: US PP31,751 P2
(45) Date of Patent: May 12, 2020

(54) ***HIBISCUS COCCINEUS* PLANT NAMED 'WHIT XXII'**

(50) Latin Name: *Hibiscus coccineus*
Varietal Denomination: Whit XXII

(71) Applicant: Lacebark, Inc., Stillwater, OK (US)

(72) Inventor: Carl E. Whitcomb, Stillwater, OK (US)

(73) Assignee: Lacebark Inc., Stillwater, OK (US)

( * ) Notice: Subject to any disclaimer, the term of this patent is extended or adjusted under 35 U.S.C. 154(b) by 0 days.

(21) Appl. No.: 16/350,958

(22) Filed: Feb. 6, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608
See application file for complete search history.

*Primary Examiner* — Anne Marie Grunberg
(74) *Attorney, Agent, or Firm* — Jeffrey L. Streets

(57) ABSTRACT

The new *Hibiscus coccineus* plant, 'Whit XXII' is characterized by a dense, dwarf, spherical growth habit, typically 20 to 30 inches in diameter covered by dense green foliage during the growing season and accentuated by large scarlet flowers dispersed over the entire form. Flowers last only one day, changing the flowering appearance of the plant daily, but flowering continues for 60 to 90 days depending on growing conditions.

6 Drawing Sheets

Genus, species: *Hibiscus coccineus.*
Varietal denomination: 'Whit XXII'.

BACKGROUND OF THE INVENTION

Field of the Invention

The present invention relates to a new and distinct variety or cultivar of the ornamental plant, *Hibiscus coccineus*, commonly known as swamp *hibiscus*, scarlet rose-mallow or marsh *hibiscus.*

Description of the Related Art

*Hibiscus coccineus* is native to the coastal regions of Virginia, the Carolinas, Georgia and north Florida along wet swampy areas including areas of mildly brackish waters, and has become naturalized along the gulf coast. However, the plant performs well in a wide variety of soils and moisture conditions far beyond its native habitat, ranging as far north as southern Pennsylvania and as far west as central Oklahoma.

*Hibiscus coccineus*, swamp *hibiscus*, flowers on new growth beginning early to midsummer, after sustained heat, and continuing into the fall. Native seedlings typically grow six to eight feet tall, often described as large and rangy and as a see-through plant since foliage is typically loose and open, with flowers produced in leaf axils, bright scarlet, solitary, three to five inches in diameter with five distinct petals. Each flower lasts only one day, typical of the genus, *Hibiscus*, but are produced in sizeable numbers.

Native seedlings are grown by some nurseries, but the loose open features limit sales, even with the plants having spectacular flowers. To date, the use of this plant in landscapes has been limited.

The tops of swamp *hibiscus* are killed by freezing weather. In the Deep South and when a freeze does not occur, tops may survive partially or in full, but this leads to an even more erratic and irregular plant. Swamp *hibiscus* produces a hardy crown at the soil surface, with abundant roots and with the return of warm soil in late spring, regrowth of a new top proceeds.

SUMMARY OF THE INVENTION

The new and distinct variety of swamp *hibiscus, Hibiscus coccineus*, which was given the cultivar name 'Whit XXII' is a compact dwarf seedling selected from a block of about 800 seedlings which were 12 generational descendants from the original plant used to begin this research.

This new and distinct *Hibiscus coccineus*, swamp *hibiscus* 'Whit XXII' was asexually reproduced near Stillwater, Okla. by softwood cuttings. The asexually reproduced plants show all the unique features of the parent. As a further test, cuttings were taken from the asexually propagated plants. These secondary cuttings rooted and grew the same as the parent, indicating that the unique features of this plant are stable through successive generations of asexual reproduction.

The new *Hibiscus coccineus* cultivar, 'Whit XXII' is characterized by a dense, dwarf, spherical growth habit, typically 20 to 30 inches in diameter, covered by dense green foliage during the growing season and accentuated by large scarlet flowers dispersed over the entire form. Flowers last only one day, changing the flowering appearance of the plant daily, but flowering continues for 60 to 90 days or more depending on growing conditions, creating a unique flower show.

In generation four following the beginning of this research, in contrast to normal growth, one dense dwarf form was observed (see FIG. 1). When two years old, flowering began and seeds were saved from this dramatically different plant. Resulting seedlings had a ratio of about 8 normal growth forms to 1 dwarf. When seeds were again saved from the dwarf forms and germinated, the resulting plants had a ratio of about 6 normal growth forms to 1 dwarf. By generation seven, seedlings from the most compact and dwarf forms had a ratio of about 2.5 normal growth forms to 1 dwarf. Seeds saved from the most compact and dwarf forms in generation nine had a ratio of 1 normal growth form to 30 dwarfs, as most seedlings were compact dwarfs, with only an occasional plant resembling the original parent (see FIG. 2). Seedlings grown from compact, dwarf plants in generations 10, 11 and 12 were all compact dwarfs. My new and unique invention of *Hibiscus coccineus*, swamp *hibiscus* named 'Whit XXII' was selected for its exceptional flowering from generation 12, a population of about 800 seedlings, all compact dwarfs.

Leaves are alternate, simple, glabrous, palmate with mostly 5 lobes, but occasionally 3 or 7, with irregularly serrate margins, overall 3.5 to 5, occasionally 6 inches long, on long petioles.

Flowers are single, borne in upper leaf axils, bright scarlet typically about 4 to 6 inches diameter, with 5 moderately variable, ovate petals ranging from cuspidate to truncate at the tip, spaced around the receptacle with only an occasional partial overlap of petals.

BRIEF DESCRIPTIONS OF THE DRAWINGS

DETAILED BOTANICAL DESCRIPTION

The following botanical description is of the new and distinct dwarf cultivar of swamp *hibiscus, Hibiscus coccineus*, which has been given the cultivar name, 'Whit XXII'. Specific color designations set forth by number designations are in accordance with The Royal Horticultural Society Colour Chart (1966). General color recitations are consistent with ordinary American color terminology.

The new swamp *hibiscus, Hibiscus coccineus*, cultivar 'Whit XXII' has not been observed under all possible environmental conditions. It is to be understood that the phenotype may vary significantly with variations in environment such as soil, temperature, light intensity and length of day without differences on the genotype of the plant. The following botanical characteristics and observations are taken from plants grown under normal outdoor conditions in north central Oklahoma, but is also consistent with plants propagated from the original parent plant growing in a field near Stillwater.

Figure 1:
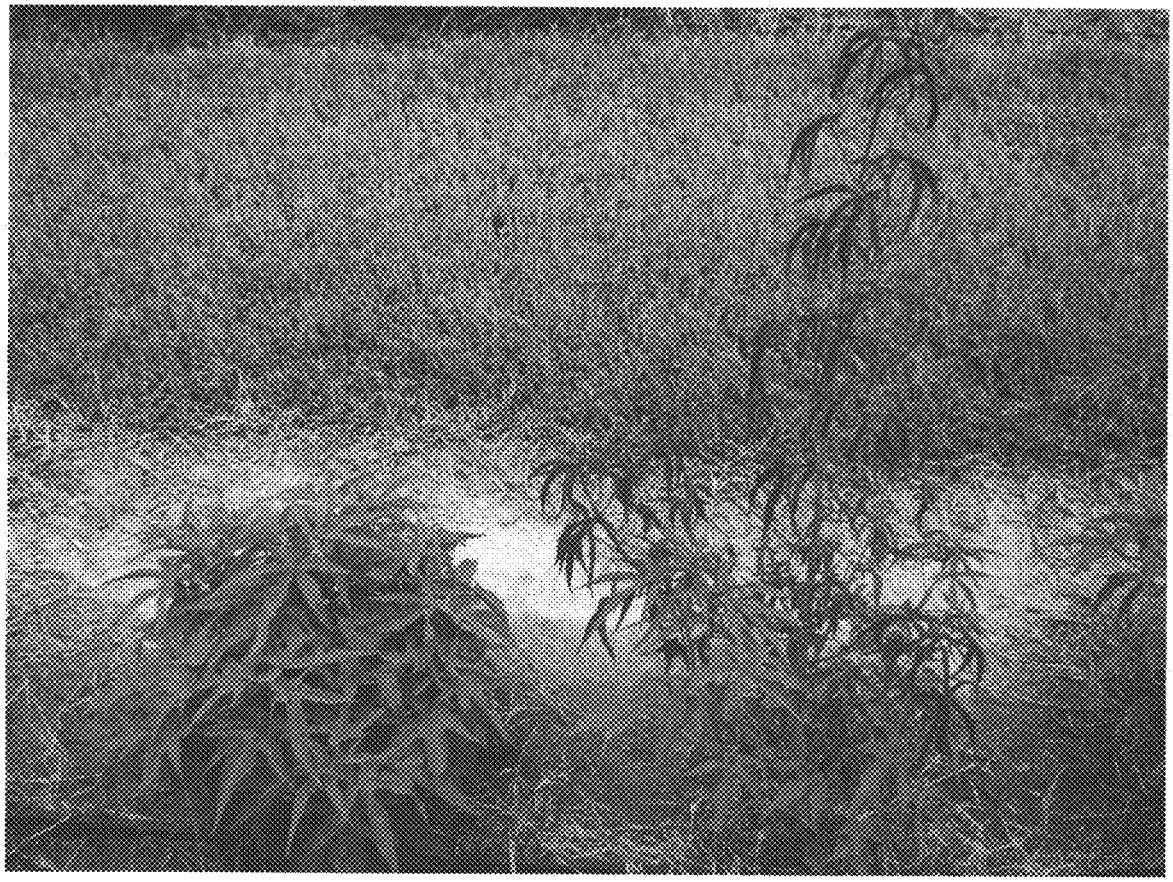
FIG. 1 is a full color photographic view of the first compact dwarf *Hibiscus coccineus* produced in generation four of this breeding program (left) versus a seedling typical of the species (right).
Figure 2:
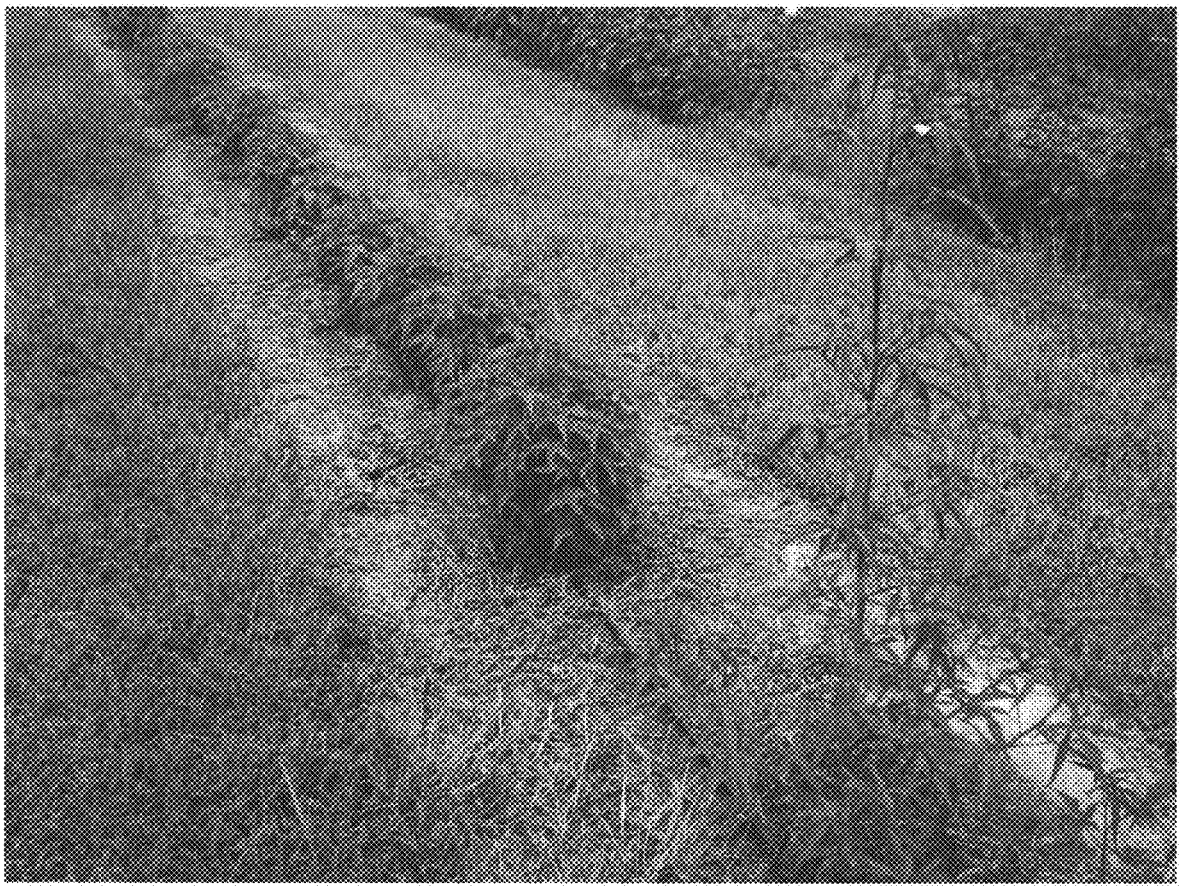
FIG. 2 is a full color photographic view of a partial row of *Hibiscus coccineus* seedlings in generation nine showing a seedling typical of the species (right) versus compact, dwarf seedlings (left).
Figure 3:
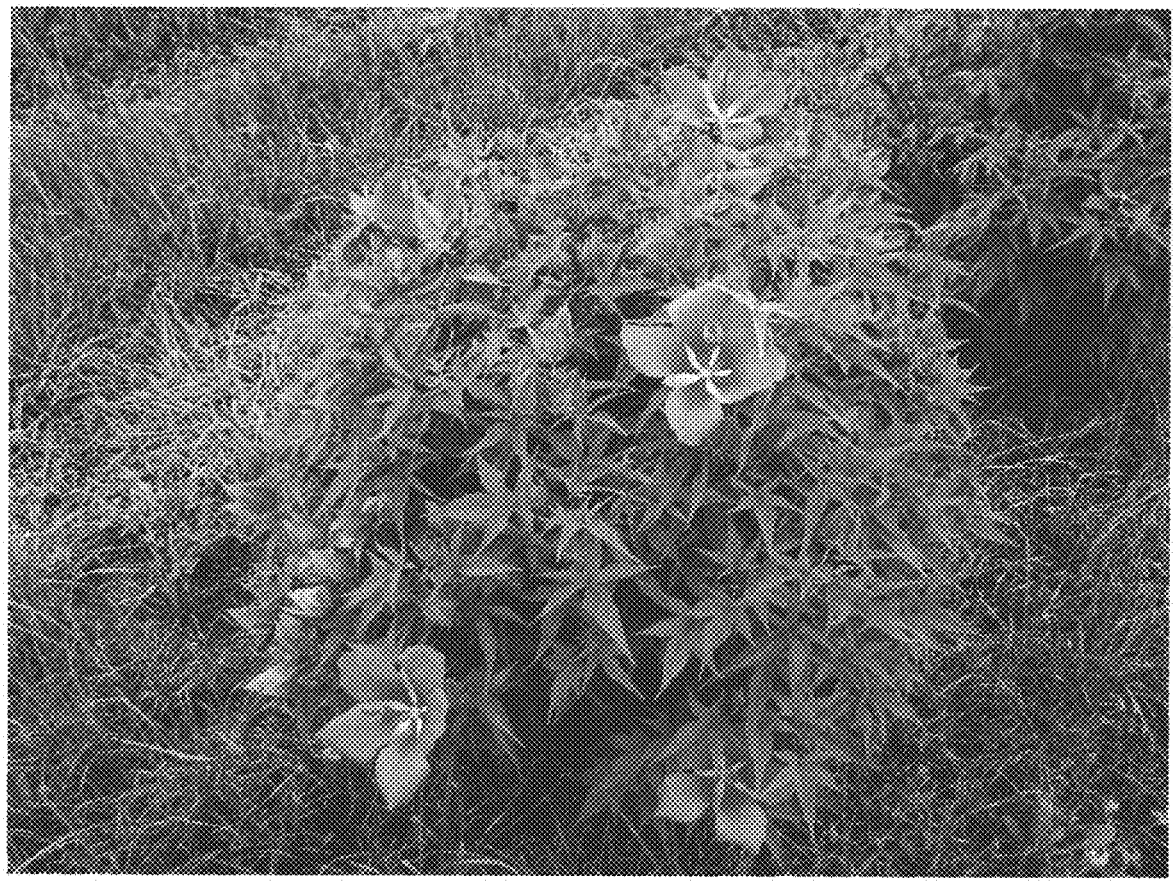
FIG. 3 is a full color photographic view of the compact dwarf *Hibiscus coccineus* plant named 'Whit XXII' showing the compact spherical form and a typical disbursement of flowers and flower buds.
Figure 4:
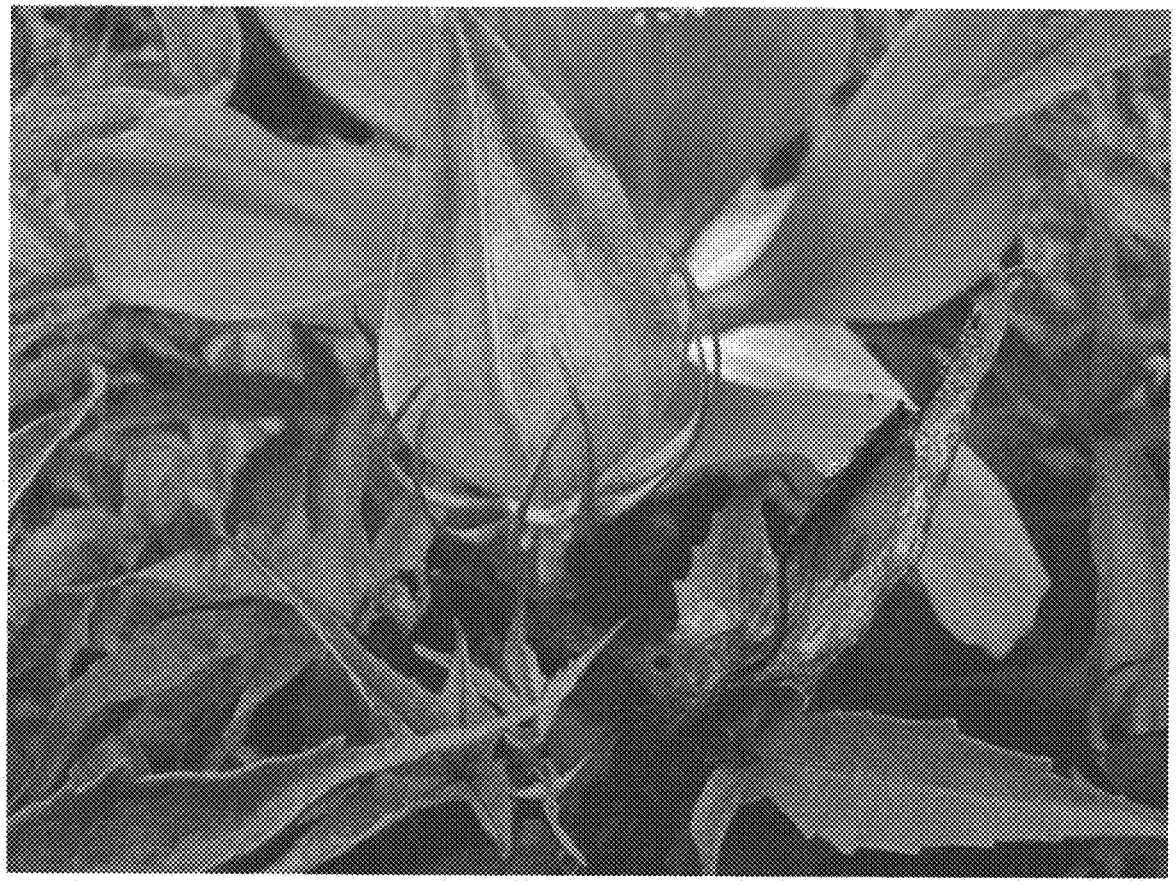
FIG. 4 is a full color photographic view of a typical flower bud of 'Whit XXII'.

The research that led to the selection of 'Whit XXII' cultivar began with seeds collected from a large seedling, roughly 9 feet tall by 4 feet wide, a very open original plant, but with spectacular flowers. Seeds were collected and planted with all seedlings looking like the original parent, until generation 4, when one seedling was distinctly dwarf and compact compared to all others. FIG. 1 shows an example of the original plant on right hand side and a 'Whit XXII' plant on left hand side. Through subsequent generations, by selecting dwarf forms as seed parents, a higher number of dwarf plants resulted in a seed population (see FIG. 2) until finally in generations 10, 11 and 12, all seedlings produced were dwarfs. The cultivar named 'Whit XXII' was selected as distinctly better (more compact, with more flowers and darker foliage) from the assortment of seedlings in generation 12. During this research, only seedlings from multiple linear generations from the original parent were used. No hybrids or seeds from other cultivars or seed parents were used.

The plant:

*Type*.—Deciduous semi-woody shrub (zones 9 and 10), herbaceous perennial (zones 6 through 8), with multiple stems and dense branching. During the growing season the plant appears as a dense woody shrub, but with the arrival of frost in the fall, the top turns brown and dies, yet the crown (bases of stems and tissues just under the soil surface) are quite cold hardy and produce a new plant when soil warms in late spring.

*Classification*.—*Hibiscus coccineus*, swamp *hibiscus* or scarlet rose-mallow.

*Growth habit*.—'Whit XXII' cultivar grows into a spherical ball each year, approx 20 to 30 inches in diameter.

*Origin*.—An open pollinated seedling selected for exceptional flowering from a block of about 800 compact dwarf seedlings which were 12 generational descendants from the original parent used to begin this research in 1987.

*Propagation*.—The plant is easy to propagate from softwood cuttings under intermittent mist with the distinguishing characteristics of the asexually propagated offspring 'Whit XXII' remaining identical to the parent.

*Size and shape*.—Growth of swamp *hibiscus* cultivar 'Whit XXII' by asexual propagated cuttings creates an irregular, spherical form, typically 20 to 30 inches tall and wide with flowers located randomly over the entire surface during the growing season. Because each flower lasts only one day and flower position the next day is different, appearance of the floral show changes daily. As the plant ages, overall width broadens slightly but height remains about the same.

*Hardiness*.—Where frosts or freezes do not occur, the tops remain and produce leaves each season. However, in hardiness zones 6 through 9 where freezes do occur, the top is killed by the first freeze, yet the crown of the plant survives and produces a new top when soils warm in late spring.

*Pests and disease*.—Resistant to feeding by both Japanese beetle and whitetail deer. No powdery mildew or other diseases have been observed during the 30 years of this breeding research.

The flowers:

*Blooming period*.—Flowering typically begins in late June or early July in north central Oklahoma, once sufficient heat has accumulated and continues until mid to late September.

Figure 5:
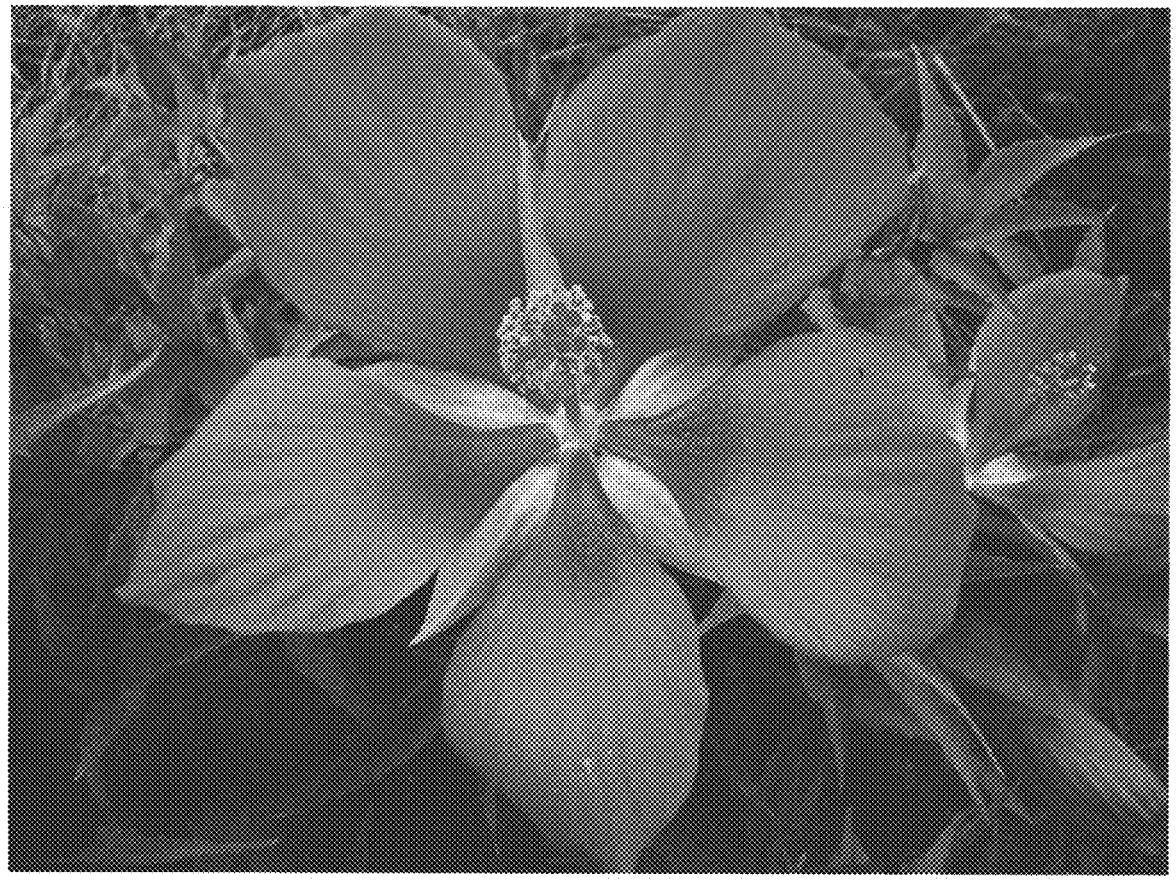
FIG. 5 is a full color photographic view of a typical scarlet red flower on the plant in FIG. 3.
Figure 6:
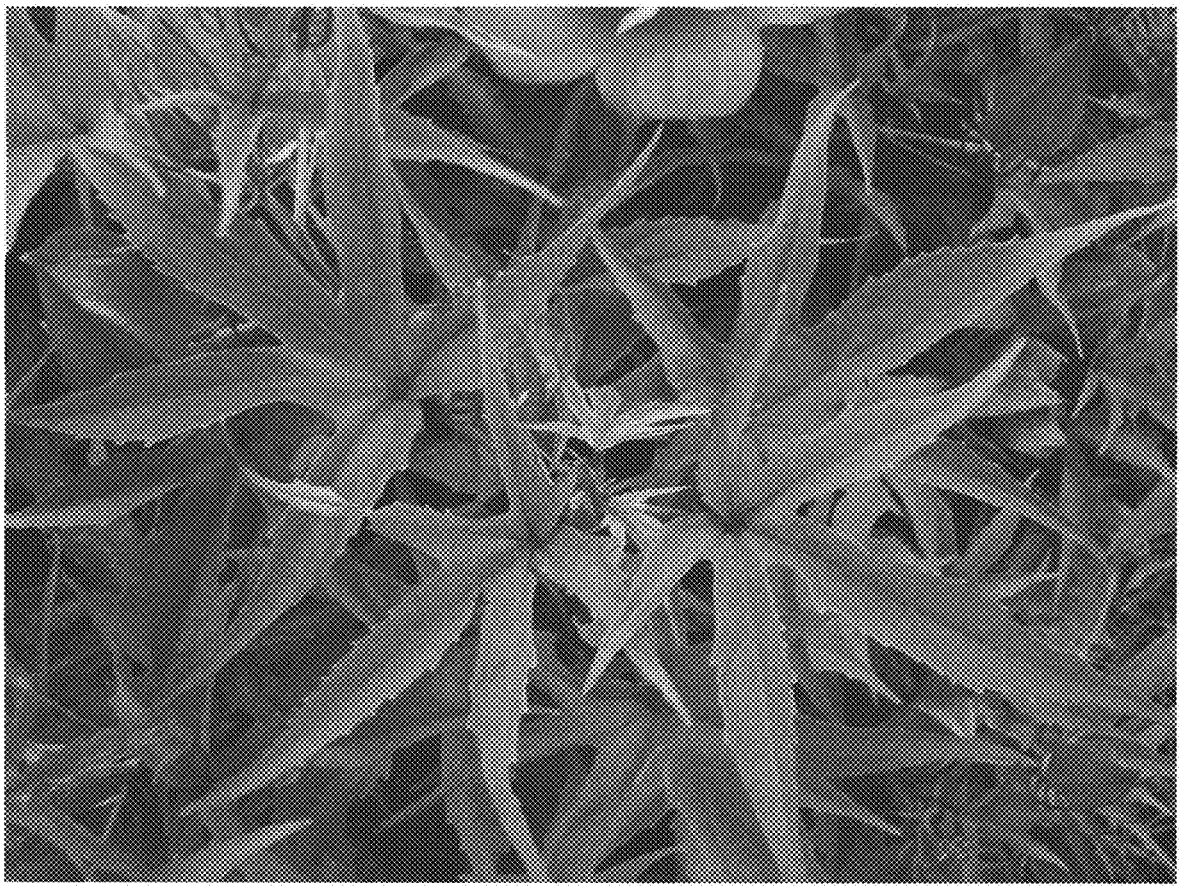
FIG. 6 is a full color photographic view of swamp *hibiscus*, 'Whit XXII' showing typical foliage ranging from very young leaves to mature foliage.

*Petals*.—Flower petals are bright scarlet red (broad outer portion approx. RHS — Red Group, 43-B or C, and darker basal portion approx. 43-A or B). The overall flower size is typically about 4 to 6 inches diameter, with 5 moderately variable, ovate, narrow ribbed petals ranging from cuspidate to truncate at the tip, spaced around the receptacle with only an occasional overlap of petals creating a propeller-like appearance. Individual petals range in size from about 2.0 to 3.2 inches long by about 1.2 to 2.75 inches wide, with individual petals varying widely in size within the same flower as shown it FIG. 5. The peduncle, the stalk supporting the flower ranges from about 0.5 inches to 2.0 inches or more. Flowers have little or no fragrance.

*Inflorescences*.—Flowers are born singly in upper leaf axils. Since leaf arrangement is alternate, flowers typically vary moderately relative to position above the foliage.

*Stamens and pistils*.—Each flower has a prominent and showy central column of stamens and styles (approx. 43-A or B) varying from about 1 to 1.75 inches long, with a collection of anthers near the top, (briefly yellow, approx. 12-B, C or D, turning a light tan in a few hours, approx. 165-C or D) located just below the typical five rounded stigma (approx. 43-A or B).

*Sepals*.—Five sepals approx. 1.25 to 1.75 inches long (approx. 147-C or D in full sun) are fused at the base to make a cup-like calyx, subtended by 10 or more bracts, variable, about half as long as the sepals. Tips of the sepals are lanceolate. When flowers are open, sepals fold back creating a saucer shape below the petal bases, the inner portion of the sepals are visible between the petals (outer portion approx. 147-C or D, gradually changing to approx. 142-C or D or 195-C or D near the center). Calyx obscures flower buds, until rapid expansion of flower petals in early morning. After petals fall, sepals resume their approximate original position, creating a papery sheath over the seed capsules.

*Seed capsules and seeds*.—Seed capsules are obovate (approx. 177-A, B or C), about 0.5 to 1 inch long and 0.5 to 0.75 inch diameter, consisting of two sections per quadrant, each containing 3 to 6 rounded seeds each about 0.125 inch diameter (approx. 177-A or B).

The foliage:

*Leaf shape*.—Leaves are palmately compound, 3 to 6 inches long, typically with five leaflets, occasionally 3 or 7, (rarely 4) on a central petiole. The leaflet width is highly variable ranging from 0.25 to 1.0 inches and variable among the leaflets of the palmate compound leaf. Leaflets are long, lanceolate to linear, with an irregular serrate margin with the central 3 leaflets longer than the basal 2. An occasional leaflet will have few or no serrations while another leaflet will be distinctly serrated.

*Leaf color*.—Upper young leaf surface in full sun approx. 147-C or D, darkening to approx. 147-A or B with maturity. Lower leaf surface is approx. 147-D or 191-A or B. Central leaf veins are purplish, approx. 187-B, C, or D. No fall color.

*Leaf texture*.—Smooth and glabrous.

*Leaf size*.—Leaves produced early in the growing season remain small, ranging from 2 to 2.5 inches, while leaves produced later in the season during warmer weather range from 3.5 to 5 inches, occasionally 6, varying with growing conditions.

The branches and bark:

*Branch color*.—Young branches and branches fully shaded are green, approx. 147-B or C while in partial sun approx. 182-A or B or with greater sun exposure, 187-A, B or C.

*Branch length*.—Branches develop from the crown during the growing season reaching typically 18 to 30 inches, with numerous variable length secondary branches.

*Branch diameter and bark*.—Branch diameter near the crown is about 0.75 to 1.5 inches, with no nodes and continuous taper to the tip. Secondary branches develop similarly, with continuous taper to the tip. Bark ranges from green when shaded to reddish purple with increased sun exposure (see branch color for details). Once a freeze occurs, branch and bark color is brown, approx. 177-A, B or C.

I claim:

1. A new and distinct variety of swamp *hibiscus* plant, *Hibiscus coccineus*, substantially as illustrated and described herein.

* * * * *